United States Patent [19]
Koslo et al.

[11] Patent Number: 5,164,379
[45] Date of Patent: Nov. 17, 1992

[54] SUCRALFATE/CYCLODEXTRIN COMPLEXES

[75] Inventors: Randy J. Koslo, West Windsor; Vincent J. Farina, Sayreville, both of N.J.

[73] Assignee: Bristol-Myers Company, New York, N.Y.

[21] Appl. No.: 734,370

[22] Filed: Jul. 15, 1991

[51] Int. Cl.$^5$ .................. A61K 31/70; A61K 31/195
[52] U.S. Cl. .............................. 514/58; 536/103; 536/118; 514/23; 514/53; 514/925; 514/926; 514/927; 514/974; 514/777
[58] Field of Search ............... 514/58, 925, 926, 927, 514/974, 777, 53, 23; 536/103, 118

[56] References Cited

U.S. PATENT DOCUMENTS

| | | | |
|---|---|---|---|
| 4,668,665 | 5/1987 | Ishihara et al. | 514/53 |
| 4,689,229 | 8/1987 | Banik | 514/925 |
| 4,834,985 | 5/1989 | Elger et al. | 424/488 |
| 4,869,904 | 9/1989 | Uekama et al. | 424/489 |
| 4,885,281 | 12/1989 | Hanstein et al. | 514/53 |
| 4,975,281 | 12/1990 | Harwood et al. | 514/53 |
| 4,980,175 | 12/1990 | Chaukin et al. | 514/53 |
| 5,066,496 | 11/1991 | Szabo et al. | 514/927 |

*Primary Examiner*—Ronald W. Griffin

[57] ABSTRACT

Complexes of sucralfate with alpha cyclodextrin, beta cyclodextrin, gamma cyclodextrin or 2-hydroxypropyl beta cyclodextrin are disclosed. Also disclosed are a process for producing complexes and compositions and a method for reducing gastric injury, employing the complexes.

17 Claims, No Drawings

SUCRALFATE/CYCLODEXTRIN COMPLEXES

FIELD OF THE INVENTION

The present invention relates to novel combinations of sucralfate and cyclodextrins believed to be in the form of a complex and use of same as gastroprotectives.

BACKGROUND OF INVENTION

Sucralfate, an aluminum salt of sucrose sulfate ester, is known to be useful in the treatment of ulcers.

Cyclodextrins are complexing agents known to form inclusion compounds with organic substances, in the solid state or in aqueous solutions. Cyclodextrins are not known to have any beneficial effect in the treatment of gastrointestinal conditions, such as ulcer.

The present inventors have discovered that, surprisingly, the combination of sucralfate and cyclodextrin affords a gastroprotective effect. Such effect is greater than the effect achieved with sucralfate alone or cyclodextrin alone. Moreover, the effect obtained with such combination is substantially greater than any possible additive effect of the activities of the components.

Data obtained by the present inventor clearly shows that the cyclodextrins of the instant invention synergize the gastroprotective effect of sucralfate.

Cyclodextrins useful in the present invention include alpha cyclodextrin, beta cyclodextrin, gamma cyclodextrin and substituted cyclodextrins, such as 2-hydroxypropyl beta cyclodextrin. Alpha cyclodextrin, beta cyclodextrin, and gamma cyclodextrin are preferred.

It is believed that the combinations of sucralfate and cyclodextrin of the present invention are complexes rather than simple mixtures.

By complex is meant an inclusion compound, inner or outer. The mechanism could involve hydrogen bonding. The present inventors have not been able to characterize the precise molecular structure. As will be shown hereinafter, the method employed in the drying step of the process used to produce the complex is a determinant of activity versus lack of activity. Freeze drying affords a substantially more active material than is obtained when the product is dried by heat (this may be indicative of an exothermic interaction). Surprisingly, air drying produces a product equivalent in activity to the sucralfate control. The fact that the process of drying is a determinant of activity versus lack of activity is consistent with complex formation, as defined herein.

The sucralfate/cyclodextrin complexes of the present invention may be prepared by a process comprising freezing, at a temperature of about −50° C. to about −70° C., an aqueous mixture of sucralfate and a cyclodextrin selected from the group consisting of alpha cyclodextrin, beta cyclodextrin, gamma cyclodextrin and 2-hydroxypropyl beta cyclodextrin. The sucralfate and the cyclodextrin are present in the mixture in an about equimolar ratio. The freezing is continued until the mixture is solidified. The solidified mixture is then freeze dried to produce the complex.

As noted heretofore it has been surprisingly discovered that sucralfate cyclodextrin complexes of the present invention provide a gastroprotective effect. More specifically they reduce the amount of damage to the stomach mucosa that is caused by irritants such as ethanol and the nonsteroidal antiinflammatory drugs, which are exemplified by aspirin, ibuprofen, naproxen, indomethacin, meclofenamate, piroxicam, phenylbutazone, and salicylates such as choline salicylate and choline magnesium trisalicylate.

There is no appreciation whatsoever in the prior art of the novel complexes of the instant invention, their preparation, or their gastroprotective effect.

The sucralfate/cyclodextrin complexes of the present invention are employed in a protective amount. More specifically, they are employed in an amount sufficient to reduce damage to the gastric mucosa which is caused by the aforementioned irritants.

The sucralfate/cyclodextrin complexes of the instant invention can be co-administered with the irritant or administered sometime prior to administration of the irritant. The optimum time lapse between administration of the sucralfate/cyclodextrin complex and administration of the irritant is readily determinable by one skilled in the art and will vary with the age, weight and physical condition of the subject. Most desirably, the sucralfate/cyclodextrin complex is co-administered with the irritant.

When the irritant is aspirin, the complex and the aspirin are most desirably employed in amounts such that the weight of sucralfate in the complex is about equal to the weight of the aspirin. When an NSAID, or other irritant, more irritating to the gastric mucosa than aspirin is to be administered, this weight relationship is adjusted upwardly by increasing the amount of complex employed. Consequently, when an NSAID, or other irritant, less irritating to the gastric mucosa than aspirin is to be administered, the weight relationship is adjusted downwardly by decreasing the amount of complex utilized.

Optimum respective amounts of various combinations of irritants and sucralfate/cyclodextrin in complexes of the instant invention are readily determinable by one skilled in the art, without the exercise of any inventive skill.

The following examples are offered to illustrate the present invention. They are not intended to limit same.

EXAMPLE 1

Preparation of Sucralfate Alpha Cyclodextrin

A. 1.0759 g (1.1059 m moles) alpha cyclodextrin were added to 250 g of reagent grade water (18 megohms resistivity) while stirring. Stirring was continued until a clear solution was obtained. 2.3076 g (1.1059 m moles) sucralfate were added to the clear solution, The resultant mixture was stirred for 3 to 4 days then shell frozen and freeze dried utilizing the procedure of part B of this Example 1.

B. The material to be shell frozen was distributed evenly in clean, dry freeze dry vessels. Only ¼ of the vessel volume was used. The vessel was capped and immersed on its side (at an angle of about 30 to 45 degrees), while manually rotating same, in SD40 alcohol which had been cooled by dry ice to a temperature of −70° C. Slow rotation of the vessel assured even distribution along the glass walls. When the shell freezing was completed (as evidenced by the absence of visible liquid) the shell frozen material was placed directly upon the freeze dryer (stabilized for an hour) for approximately 2 days to assure thorough drying. The freeze dried material, so produced, was then collected in tared vessels.

EXAMPLE 2

Preparation of Sucralfate Beta Cyclodextrin

A. 1.2552g (1.1059 m moles) beta cyclodextrin were added to 250g of reagent grade water (18 megohms resistivity) while stirring. Stirring was continued until a clear solution was obtained. 2.3076g (1.1059 m moles) sucralfate were added to clear solution. The resultant mixture was stirred for 3 to 4 days then shell frozen and freeze dried utilizing the procedure of part B of Example 1.

EXAMPLE 3

Preparation of Sucralfate Gamma Cyclodextrin

A. 1.4332g (1.1059 m moles) gamma cyclodextrin were added to 250g of reagent grade water (18 megohms resistivity) while stirring. Stirring was continued until a clear solution was obtained. 2.3076 g (1.1059 m moles) sucralfate were added to the clear solution. The resultant mixture was stirred for 3 to 4 days then shell frozen and freeze dried utilizing the procedure of part B of Example 1.

EXAMPLE 4

Preparation of Sucralfate 2-hydroxypropyl Beta Cyclodextrin

A. 1.6589 g (1.1059 m moles) 2- hydroxypropylbetacyclodextrin were added to 250 g of reagent grade water (18 megohms resistivity) while stirring. Stirring was continued until a clear solution was obtained. 2.3076 g (1.1059 m moles) sucralfate were added to the clear solution. The resultant mixture was stirred for 3 to 4 days then shell frozen and freeze dried utilizing the procedure of part B of Example 1.

The following Example 5 illustrates an alternative method of preparing the novel complexes of the present invention:

EXAMPLE 5

Sucralfate beta cyclodextrin

A. 2.5104 g (2.2118 m moles) beta cyclodextrin were added to 500 of reagent grade water (18 megohms resistivity) while stirring. Stirring was continued until a clear solution was obtained. 4.6154 g (2.2118 m moles) sucralfate were added to the clear solution. The resultant mixture was stirred for 6 days then rotoevaporated at 50° C.

B. 2.5104 g (2.2118 m moles) beta cyclodextrin were added to 500 g of reagent grade water (18 megohms resistivity) while stirring. Stirring was continued until a clear solution Was obtained. 4.6154 g (2.2118 m moles) sucralfate were added to the clear solution. The resultant mixture was stirred for 6 days then rotoevaporated at 80° C.

C. 1.2553 g (1.1059 m moles) beta cyclodextrin were added to 250 g of reagent grade water (18 megohms resistivity) while stirring. Stirring was continued until a clear solution was obtained. 2.3077 g (1.1059 m moles) sucralfate were added to the clear solution. The resultant mixture was stirred for 1 hour and then evaporated at room temperature for 2 days.

EXAMPLE 6

A. Gastroprotective efficacy was determined by means of the following canine endoscopic test method:

Pedigreed beagles of both sexes were fasted overnight. At zero time, the stomach of each animal was endoscopically examined to assure a normal mucosa. Encapsulated formulations of test material plus aspirin (975 mg/dose), prepared immediately before the test, were administered orally and flushed in with 50 ml water. Two and four hours after administration of the test material, the dogs' stomachs were endoscopically reexamined. Gastric irritation was scored on a scale of 0 to 7. 0 reflecting a normal stomach and 7 reflecting massive hemorrhagic damage. A sample of gastric fluid was obtained from the antrum. General appearance and pH of the sample were noted. Severity of bleeding score was calculated as mean bleed severity.

B. Utilizing the canine endoscopic test procedure of part A of this Example 6, the complexes of Examples 1 through 5 were evaluated. Aspirin (975 mg); a combination of aspirin (975 mg) and freeze dried sucralfate (980 mg); and a combination of aspirin (975 mg) and alpha cyclodextrin (6.25 g) were similarly evaluated, for comparative purposes.

The results are set forth in the following Table I. Percent protection was calculated as follows:

TABLE 1

| Treatment | Mean 2 Hr. Irritation Score | % Protection |
|---|---|---|
| Aspirin 0.975 g | 5.45 ± 0.14 | 0 |
| Aspirin 0.975 g + Sucralfate 0.980 g | 4.5 ± 0.35 | 17.4 ± 9.4 |
| Aspirin 0.975 g + freeze dried sucralfate 0.980 g | 4.5 ± 0.50 | 17.4 ± 9.2 |
| Aspirin 0.975 g + Alpha cyclodextrin 6.25 g | 4.5 ± 0.65 | 17.4 ± 11.8 |
| Aspirin 0.975 g + freeze dried Sucralfate alpha cyclodextrin 1.545 g | 1.5 ± 0.5 | 72.5 ± 9.2 |
| Aspirin 0.975 g + freeze dried Sucralfate beta cyclodextrin 1.595 g | 0.5 ± 0.5 | 90.8 ± 9.2 |
| Aspirin 0.975 g + freeze dried Sucralfate gamma cyclodextrin 1.800 g | 2.0 ± 1.0 | 63.3 ± 18.3 |
| Aspirin 0.975 g + freeze dried Sucralfate 2-hydroxypropyl beta cyclodextrin 1.850 g | 2.0 ± 1.0 | 63.3 ± 18.3 |
| Aspirin 0.975 g + Rotoevaporated at (50° C.) Sucralfate beta cyclodextrin 1.882 g | 4.0 ± 1.0 | 26.6 ± 18.3 |
| Aspirin 0.975 g + Rotoevaporated at (80° C.) Sucralfate beta cyclodextrin 1.583 g | 4.0 ± 1.0 | 26.6 ± 18.3 |
| Aspirin 0.975 g + Evaporated at room temperature (23° C.) Sucralfate beta cyclodextrin 1.7849 g | 4.5 ± 0.50 | 17.4 ± 9.2 |

The data of Table 1 clearly demonstrates that the method of preparation of the complex is important. Product produced by freeze drying affords a substantially greater level of protection. (e.g. 90.8±9.2 vs 26.6±18.3). This is clearly indicative of the formation of a sucralfate/cyclodextrin complex when the freeze drying method is employed and the formation of a simple mixture when rotoevaporation is utilized.

The results of Table 1 clearly demonstrate that the sucralfate cyclodextrins of the present invention are vastly superior to sucralfate in protecting against NSAID induced gastric irritation.

It should be noted that, in Table 1, magnified deviations from the mean are attributable due to use of fewer animals (because of the inventors desire to employ as few animals as possible) and to dose response effects.

While our data demonstrates that co-administration of the gastroprotective complexes disclosed herein with the gastric irritant is effective to protect the gastric mucosa, our experience has shown that this is a clear indicator that the novel complexes of this invention will also have gastroprotective effect when administered sometime prior to administration of the gastric irritant. For example, one can administer a gastroprotective amount of a complex according to this invention at several spaced intervals over the course of a day; each preceding the administration of a gastric irritant such as an NSAID by, for example, an hour.

The novel complexes of sucralfate and cyclodextrins of the instant invention may be administered to a mammal requiring treatment with a gastric irritant such as, a nonsteroidal antiinflammatory drug ("NSAID"), e.g. aspirin, ibuprofen, etc., in dosage forms well known to the skilled artisan for oral administration. For example, the complexes may be administered by capsule, tablet, powder, liquid preparations, etc.

Chewable and/or swallowable tablets are today widely accepted and are preferred.

The following Examples 7-10 serve to illustrate, but are not intended to limit the scope of such compositions. The compositions are prepared according to the following general procedure:

General Procedure

A first mixture consisting of a commercially available mixture of aspirin and 10% starch granulation (12/50 mesh) and a second mixture, prepared by mixing a complex of the present invention with corn starch in a suitable mixer, are tabletted in a conventional two layer tablet press equipped with 0.5 inch flat faced beveled edge punches. The tablets have one layer consisting of aspirin and the 10% starch granulation (12 /50 mesh) a nd another layer consisting of the sucralfate/cyclodextrin complex of the invention and corn starch disintegrant.

Using this procedure, the following chewable or swallowable tablet formulations are prepared:

| Tablet Ingredients | Example 7 | Example 8 | Example 9 | Example 10 |
|---|---|---|---|---|
| Layer #1 | | | | |
| Aspirin | 325 mg | 325 mg | 325 mg | 325 mg |
| 10% Starch Granulation (12/50 mesh) | 36 mg | 36 mg | 36 mg | 36 mg |
| Layer #2 | | | | |
| Sucralfate/Alpha Cyclodextrin Complex | 515 mg | — | — | — |
| Sucralfate/Beta Cyclodextrin Complex | — | 532 mg | — | — |
| Sucralfate/Gamma Cyclodextrin Complex | — | — | 600 mg | — |
| Sucralfate/2-hydroxypropyl Beta Cyclodextrin Complex | — | — | — | 617 mg |
| Corn Starch Disintegrant | 51 mg | 53 mg | 60 mg | 61 mg |

What is claimed is:

1. A sucralfate/cyclodextrin complex selected from the group consisting of sucralfate/alpha cyclodextrin, sucralfate/beta cyclodextrin, sucralfate/gamma cyclodextrin, sucralfate/ 2-hydroxypropyl beta cyclodextrin and mixtures thereof.

2. The complex as claimed in claim 1, wherein the complex is the sucralfate/alpha cyclodextrin complex.

3. The complex as claimed in claim 1, wherein the complex is the sucralfate/beta cyclodextrin complex.

4. The complex as claimed in claim 1, wherein the complex is the sucralfate/gamma cyclodextrin complex.

5. The complex as claimed in claim 1, wherein the complex is the sucralfate/2-hydroxypropyl beta cyclodextrin complex.

6. A method for reducing injury to gastric mucosa of a mammal when the mucosa is contacted with an irritant comprising administering to such mammal a mucosal injury reducing amount of a sucralfate/cyclodextrin complex selected from the group consisting of sucralfate/alpha cyclodextrin, sucralfate/beta cyclodextrin, sucralfate/gamma cyclodextrin, sucralfate/ 2-hydroxypropyl beta cyclodextrin and mixtures thereof.

7. The method as claim in claim 6, wherein the complex is co-administered with the irritant.

8. The method as claimed in claim 6, wherein the complex is administered prior to contact of the mucosa by the irritant.

9. The method as claimed in claim 6, wherein the irritant is a nonsteroidal antiinflammatory agent.

10. The method as claimed in claim 9, wherein the nonsteroidal antiinflammatory agent is selected from the group consisting of aspirin, ibuprofen, naproxen, indomethacin, meclofenamate, piroxicam, phenylbutazone, choline salicylate and choline magnesium trisalicylate.

11. The method as claimed in claim 10, wherein the irritant is aspirin.

12. The method as claimed in claim 6, wherein the irritant is ethanol.

13. A composition having reduced propensity for causing injury to mammalian gastric mucosa comprising a normally gastric mucosal injury causing amount of a gastric irritant and a gastric mucosal protective amount of a sucralfate/cyclodextrin complex selected from the group consisting of sucralfate/alpha cyclodextrin, sucralfate/beta cyclodextrin, sucralfate/gamma cyclodextrin, sucralfate/ 2-hydroxypropyl beta cyclodextrin and mixtures thereof.

14. The composition as claimed in claim 13, wherein the gastric irritant is a nonsteroidal antiinflammatory agent.

15. The composition as claimed in claim 14, wherein the nonsteroidal antiinflammatory agent is selected from the group consisting of aspirin, ibuprofen, naproxen, indomethacin, meclofenamate, piroxicam, phenylbutazone, choline salicylate and choline magnesium trisalicylate.

16. The composition as claimed in claim 15, wherein the irritant is aspirin.

17. A process for producing a sucralfate/cyclodextrin complex as claimed in claim 1, comprising freezing, at a temperature of about −50° C. to about −70° C., an aqueous mixture of sucralfate and a cyclodextrin selected from the group consisting of alpha cyclodextrin, beta cyclodextrin, gamma cyclodextrin and 2-hydroxypropyl beta cyclodextrin, the sucralfate and the cyclodextrin being present in an about equimolar ratio, the freezing being continued until the mixture is solidified, then freeze drying the solidified mixture, whereby said complex is produced.

* * * * *